United States Patent [19]

Taylor

[11] 4,425,193

[45] Jan. 10, 1984

[54] ELECTROCHEMICAL PREDICTION OF CORROSION SUSCEPTIBILITY OF ZIRCONIUM-BASE ALLOYS

[75] Inventor: Dale F. Taylor, Schenectady, N.Y.

[73] Assignee: General Electric Company, Schenectady, N.Y.

[21] Appl. No.: 353,308

[22] Filed: Mar. 1, 1982

[51] Int. Cl.$^3$ .................. G01N 27/46; G01N 27/30
[52] U.S. Cl. ................................. 204/1 T; 204/404
[58] Field of Search .................. 204/1 C, 195 C, 404

[56] References Cited

U.S. PATENT DOCUMENTS

| | | | |
|---|---|---|---|
| 3,486,996 | 12/1969 | Annand | 204/195 C |
| 4,238,298 | 12/1980 | Tsuru et al. | 204/1 T |
| 4,256,542 | 3/1981 | Tytgat | 204/1 T |

OTHER PUBLICATIONS

J. Postlethwaite et al., "Electrochemical Flow Cell for Elevated Temperature/Pressure Aqueous Corrosion Studies", *Corrosion Science*, vol. 10, pp. 885–890, (1970).

Primary Examiner—Aaron Weisstuch
Attorney, Agent, or Firm—Leo I. MaLossi; James C. Davis, Jr.; James Magee, Jr.

[57] ABSTRACT

An electrochemical apparatus and a testing procedure are described for predicting the susceptibility of certain zirconium-base alloys to nodular corrosion in boiling water reactor environments. A chemically polished pre-determined area of the surface of the zirconium-base alloy is made the anode in an electrochemical cell. A constant direct current (d-c) having an alternating current (a-c) superimposed thereon is applied to the cell and the quadrature component of the a-c cell voltage is monitored in order to measure the value of the depth of the minimum occurring in the quadrature component of the a-c cell voltage-versus-time relationship after a d-c cell voltage of at least eight volts has been reached. The application of a-c to the cell is stopped and the constant d-c previously applied is decreased by a a step-change to a constant value providing a reduction of at least one-half in the current density. The d-c cell voltage response to this step-change exhibits a transient decrease and the d-c cell voltage response as a function of time is monitored until the cell voltage again starts to rise in order that the magnitude of this transient can be measured. A constant d-c current is then re-applied to the cell and the degree of non-linearity occurring in the relationship between d-c cell voltage and time is measured. The magnitude of a minimum in the quadrature component of the a-c cell voltage, the magnitude of the transient in the d-c cell voltage response to the step-change in d-c current and the degree of non-linearity displayed in the relationship between d-c cell voltage and time (or some other parameter, which directly relates to time) are compared to standardized values and an assessment, or determination, of the corrosion susceptibility of the sample can be made based upon this comparison.

30 Claims, 8 Drawing Figures

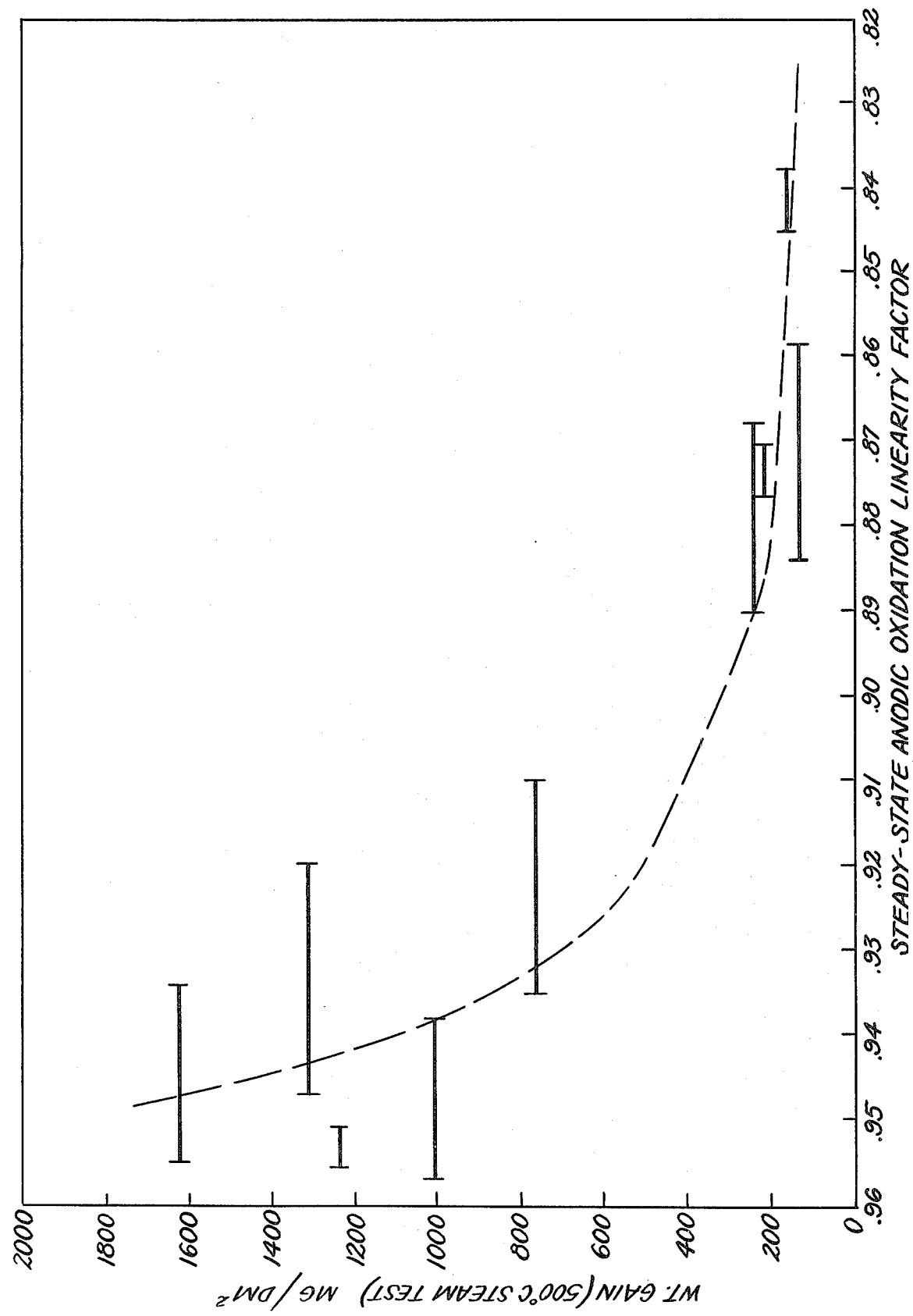

ELECTROCHEMICAL PREDICTION OF CORROSION SUSCEPTIBILITY OF ZIRCONIUM-BASE ALLOYS

The present invention relates to the nodular corrosion phenomena which develop on Zircaloy components in boiling water reactor environments and to a lesser extent on Zircaloy components in pressurized water reactors and presents apparatus and procedures for effective screening of these materials in order to predict whether or not particular samples will be susceptible to nodular corrosion. The zirconium-base alloys with which this invention is concerned typically contain, in addition to zirconium, small amounts of tin, iron, chromium and nickel. The incidence of nodular corrosion is of particular concern in fuel cladding, because, when present, the resulting thick, spalling oxide reduces heat transfer efficiency and could produce hot spots. In view of the impracticability of utilizing in-reactor tests, the need for a reliable ex-reactor test has long been recognized.

BACKGROUND OF THE INVENTION

Efforts to correlate the nodular corrosion of Zircaloys with high-temperature, high-pressure steam autoclave tests have been described in the paper, "Nodular Corrosion of the Zircaloys" by Johnson, Jr. and Horton [Symposium, Zirconium in the Nuclear Industry-Quebec, Canada, Aug. 10–12, 1976] and the article, "A Preliminary Correlation Between the Accelerated Corrosion of Zircaloy In BWR'S and In High Temperature, High Pressure Steam" by Urquhart and Vermilyea [*Journal of Nuclear Materials*, Vol. 62, No. 1, October, 1976, pp. 111–114-North-Holland Publishing Company, Amsterdam]. The several factors which promote the attack on Zircaloys in-reactor resulting in nodule formation appear to be high system pressure, radiation, flow disturbances and oxygenated conditions. As seen in these articles, a high-temperature (about 500° C.), high-pressure (about 1500 psi) steam environment produces a reasonable simulation of the BWR corrosion phenomena although no explanation exists for the correlation. One of the disadvantages of this test is the period of time required, usually from 22 to 24 hours.

DESCRIPTION OF THE INVENTION

Apparatus and a testing procedure have been developed for collecting and correlating certain electrochemical kinetic information relating to the efficiency of anodic oxide film formation on the surfaces of zirconium-base alloys such as Zircaloy-2. In the practice of this invention, a chemically polished pre-determined area of the surface of the zirconium-base alloy is made the anode in an electrochemical cell. A constant direct current (d-c) having an alternating current (a-c) superimposed thereon is applied to the cell and the quadrature component of the a-c cell voltage is monitored in order to measure the value of the depth of the minimum occurring in the quadrature component of the a-c cell voltage-versus-time relationship after a d-c cell voltage of at least eight volts has been reached. The application of a-c to the cell is stopped and the constant d-c previously applied is decreased by a step-change to a constant value, providing a reduction of at least one-half in the current density. The d-c cell voltage response to this step-change exhibits a transient decrease and the d-c cell voltage response as a function of time is monitored until the cell voltage again starts to rise in order that the magnitude of this transient can be measured. A constant d-c current is then re-applied to the cell and the degree of non-linearity occurring in the relationship between d-c cell voltage and time is measured. At this point, a measure of three electrochemical characteristics of the anode surface will have been obtained; namely, the magnitude of a minimum in the quadrature component of the a-c cell voltage, the magnitude of the transient in the d-c cell voltage response to the step-change in d-c current and the degree of non-linearity displayed in the relationship between d-c cell voltage and time (or some other parameter, which directly relates to time). These values are then compared to standardized values and an assessment, or determination, of the corrosion susceptibility of the sample can be made based upon this comparison.

In a simpler version of this procedure, there is no superimposition of a-c current and, consequently, no measure of the quadrature component. Reliance is placed for the assessment of corrosion susceptibility upon the transient produced in the d-c cell voltage response by the step-change in d-c current, and the extent of non-linearity in the d-c cell voltage-versus-time relationship at higher d-c cell voltages.

In its most generic sense, the process of this invention contemplates a non-destructive electrochemical test for predicting the ability of a zirconium-base alloy to resist nodular corrosion in a water-cooled nuclear reactor during normal operation, in which the test surface area of the alloy is made the anode in an electrochemical cell; constant d-c current, alone or with a superimposed constant a-c current (RMS), is applied to the cell as appropriate; at least one electrochemical kinetic parameter of the alloy selected from the group consisting of (1) the minimum in the a-c quadrature voltage component of the a-c cell voltage, (2) the magnitude of the transient in the d-c cell voltage-versus-time relationship and (3) the degree of non-linearity in the d-c cell voltage-versus-time relationship is determined and compared to a standard.

The relationship between the electrochemical kinetic parameter information and nodular corrosion susceptibility is as follows:
(a) Increasing depth of the minimum occurring in the a-c quadrature voltage component reflects increasing corrosion susceptibility;
(b) Increasing magnitude of the transient occurring in the d-c cell voltage/time relationship indicates increasing corrosion susceptibility; and
(c) Increasing degree of non-linearity indicates decreasing corrosion susceptibility.

Apparatus for conducting the method including the determination of the depth of the minimum occurring in the quadrature component of the a-c cell voltage-versus-time relationship comprises, in combination, means adapted to releasably cooperate with a pre-determined portion of the surface area of a zirconium-base alloy body to be tested to define a liquid-tight volume therewith. Inlet and outlet means in flow communication with the liquid-tight volume are provided in order to selectively introduce and remove electrolyte. The defining means also includes electrically conducting structure, which will be spaced from, and electrically insulated from, the pre-determined area of the alloy body when the defining means is disposed in cooperative relationship with surface area of the alloy body. Means electrically connected to the electrically conducting structure and also adapted to be electrically connected to the pre-determined area is provided for supplying constant d-c current between the structure and the surface area. Depending upon the number of electrochemical parameters to be determined, the d-c current supply means is to have control capability to enable the application of current at one or more levels of intensity. When the liquid-tight volume is occupied by an electrolyte and constant d-c current is applied between the electrically conducting structure and the pre-determined area of the alloy body, means electrically connected to the electrically conducting structure and the pre-determined area sense and record the d-c voltage occurring therebetween as a function of time. Means are supplied for selectively applying an a-c current to the constant d-c current supply means, resulting in the superimposition of an a-c current on the d-c current output of the d-c current supply means. Further, means electrically connected to the electrically conducting structure and also adapted to be electrically connected to the predetermined area are provided for sensing and recording the a-c quadrature component of the a-c voltage occurring as a function of time between the electrically conducting structure and the pre-determined area when d-c current with superimposed a-c current is applied therebetween. In addition, the means for sensing and recording the a-c quadrature component of the a-c voltage is electrically connected to the a-c current applying means in order to receive a reference a-c signal therefrom.

The apparatus for determining corrosion susceptibility by the simpler method, which does not include the determination of the a-c quadrature component of the a-c cell voltage, differs from the apparatus described hereinabove in that it does not employ a-c current applying means nor means for sensing and recording the a-c quadrature component.

Although the invention is broadly applicable to various alloy body shapes, the prime application of this invention is to bodies of tubular-shape, i.e. tubeshell and fuel cladding prepared therefrom.

Although in many instances the terminology used herein refers to changes in one or another electrochemical kinetic parameter "as a function of time", it is to be understood that this term is not restricted to the use specifically of time as a variable, but also includes in the case of the a-c quadrature of the a-c cell voltage, the use of d-c cell voltage, which has a direct relationship to time.

BRIEF DESCRIPTION OF THE DRAWINGS

The features of this invention believed to be novel and unobvious over the prior art are set forth with particularity in the appended claims. The invention itself, however, as to the organization, method of operation and objects and advantages thereof, may best be understood by reference to the following description taken in connection with the accompanying drawings wherein:

FIGS. 6, 7 and 8 present graphic illustrations of one manner in which standardized values can be established for each electrochemical kinetic parameter determinable in the practice of this invention in order to assess the corrosion susceptibility of a given zirconium-base alloy body.

MANNER AND PROCESS OF MAKING AND USING THE INVENTION

Figure 1:
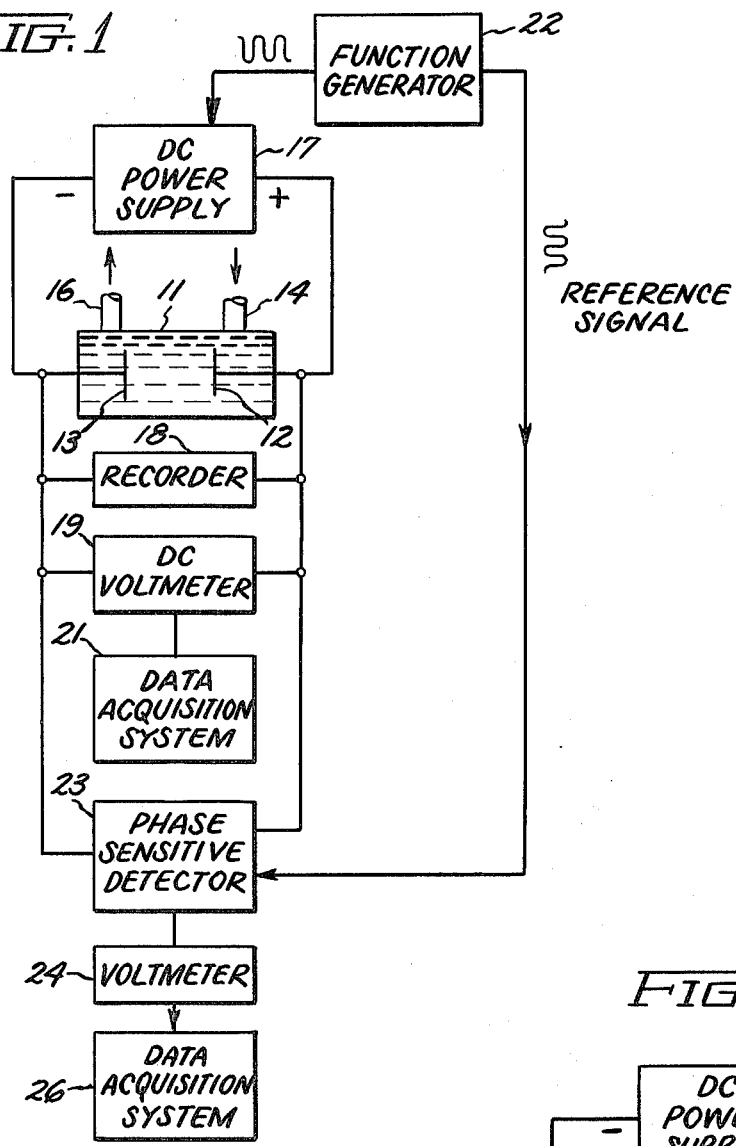
FIG. 1 is a schematic representation of apparatus for accumulating the full set of electrochemical kinetic information, including the determination of the a-c quadrature voltage component of the a-c cell voltage occurring as a function of time.

The rapid, non-destructive room-temperature electro-chemical test procedure of this invention typically employs the apparatus illustrated in FIG. 1. The corrosion susceptibility test itself can be conducted in less than about thirty minutes and is expected to be adaptable to the provision of an automated testing and decision-making installation. The zirconium-base alloys to which the procedure of this invention can function as a screening test are those typically containing small quantities of tin, iron, chromium and nickel (e.g., Zircaloy-2).

Figure 2:
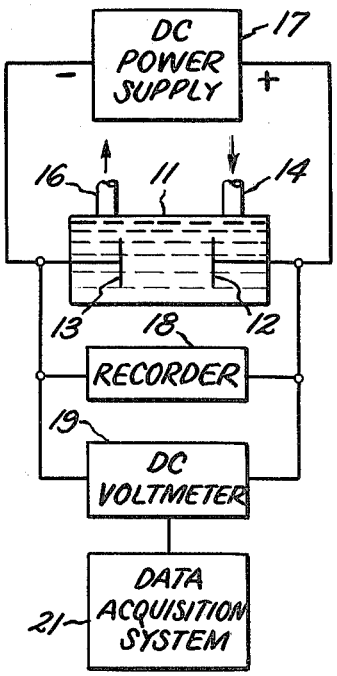
FIG. 2 is a schematic view of apparatus for practicing a simpler process of this invention.

In order to practice this invention, it is necessary to establish an electrochemical cell 11 within which a reproducible and constant (i.e., good surface definition) surface area of the alloy body being tested is made the anode. This surface area-anode is schematically represented in FIGS. 1 and 2 by numeral 12. The counterelectrode schematically illustrated therein is identified by numeral 13. The preferred device for defining such an electrochemical cell is described in FIG. 3 and will be described hereinafter. In any event, it is important that the volume defined by whatever device is employed to cooperate with surface area of the alloy body to form the electrochemical cell, be liquid-tight in order that results will be reproducible. Electrolyte, preferably dilute sulfuric acid, is introduced via cell inlet means 14 and this electrolyte after traversing the cell volume leaves cell 11 through outlet 16. Counterelectrode 13 can be the metal portion of a housing, as in the case of the device shown in FIG. 3, or may be supported from the wall of the device in the case of a housing made of electrically insulating material, such as glass. An example of the latter form of counterelectrode would be a metallic screen.

When electrolytic cell 11 has been properly defined and provided with electrolyte, connections are made to electrodes 12 and 13 from d-c power supply 17 (e.g., Model 173, Princeton Applied Research Potentiostat/Galvanostat) as shown in order to impose a constant d-c current on cell 11. When imposed, the d-c current causes electrode 12 to undergo anodic oxidation and, as a result, the d-c voltage across cell 11 between electrodes 12 and 13 increases as a function of time. The d-c power supply 17 is provided with control capability whereby the d-c current supplied thereby can be reduced sharply by a step decrease to a lower value of d-c current, or increased in the same way, when desired. The effect of this step-change on the d-c cell voltage is one of the parameters providing information on the susceptibility of the alloy body to nodular corrosion.

Figure 4:
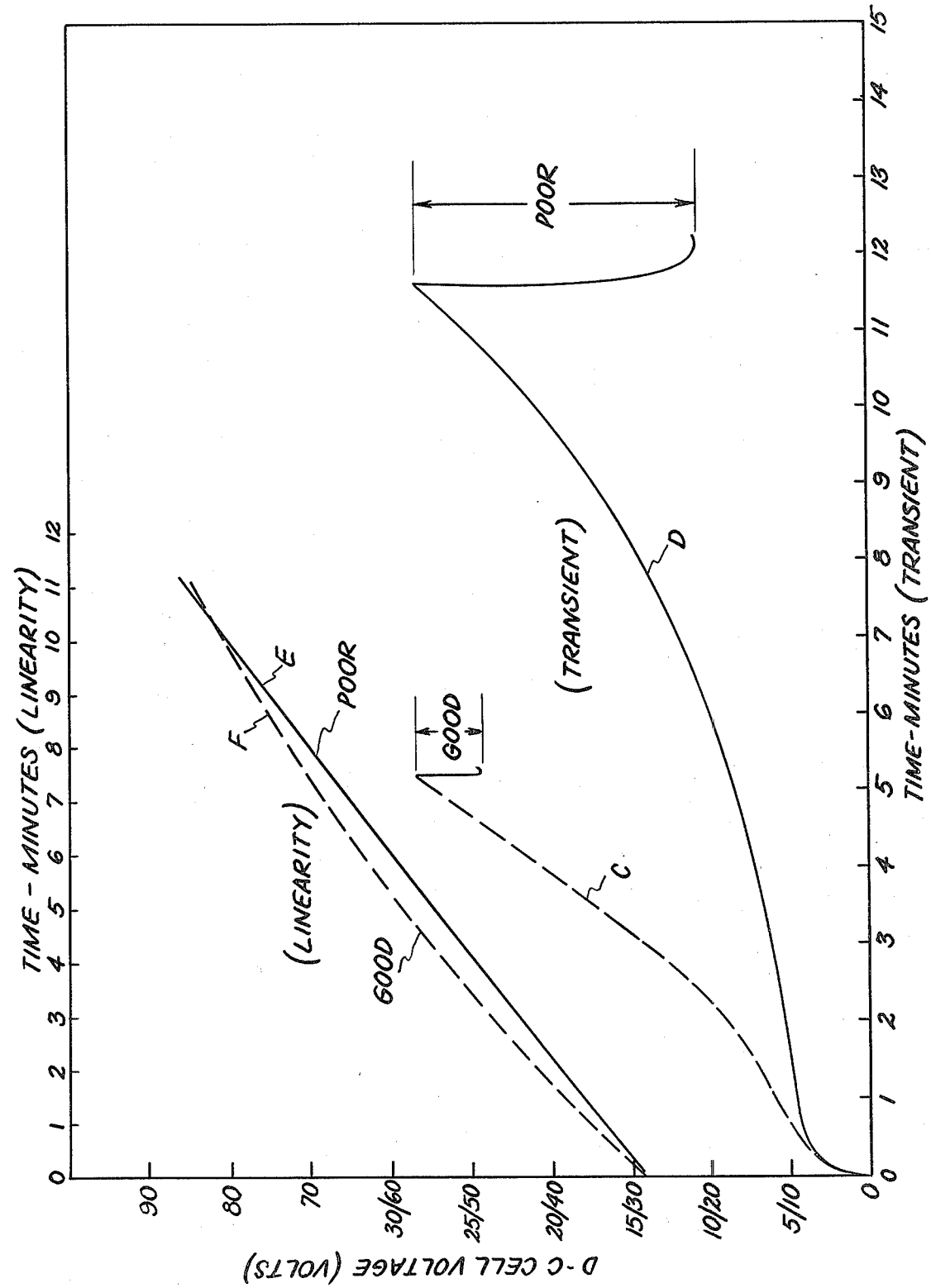
FIGS. 4 and 5 display typical electrochemical kinetic output curves that may be obtained in the practice of this invention.

Apparatus for both analog and digital recordings of the change in d-c cell voltage with time are provided in the apparatus of FIGS. 1 and 2 in order to obtain both a graphic representation thereof (as is shown in FIG. 4) and to use the stored digital information to perform calculations for determining the degree of non-linearity in the d-c cell voltage/time relationship. This arrangement is representative of that actually used; however, this redundancy can be avoided by using equipment for digital recording capable of taking readings about one millisecond apart (so as not to miss the high and low extremes of the d-c cell voltage transient caused by the step-change) and then printing out a graphic representation thereof. Thus, recorder 18 (e.g., Houston Instrument-Omnigraphic 2000 Recorder, with Type 6 time base) senses the d-c voltage across cell 11 and generates a graph (see FIG. 4, lower graphs) reflecting the change in d-c cell voltage with time on an X-Y recorder. In addition, voltmeter 19 (e.g., Fluke Model A502A Digital Multimeter) senses the same information and stores the information in data acquisition system 21 (e.g., North Star Horizon Computer interfaced with a Texas Instruments, Inc. Silent 700 ASR Electronic Data Terminal). The computer preferably is also programmed to calculate the slope of the d-c cell voltage/time relationship at specified points (e.g., at 35 volts and 75 volts) and then determine the ratio of the slopes (e.g., the slope at 75 v. divided by the slope at 35 v.). The resulting value provides a quantitative indication of non-linearity, or curvature (see FIG. 4, upper graphs) of the voltage/time response.

Figure 5:
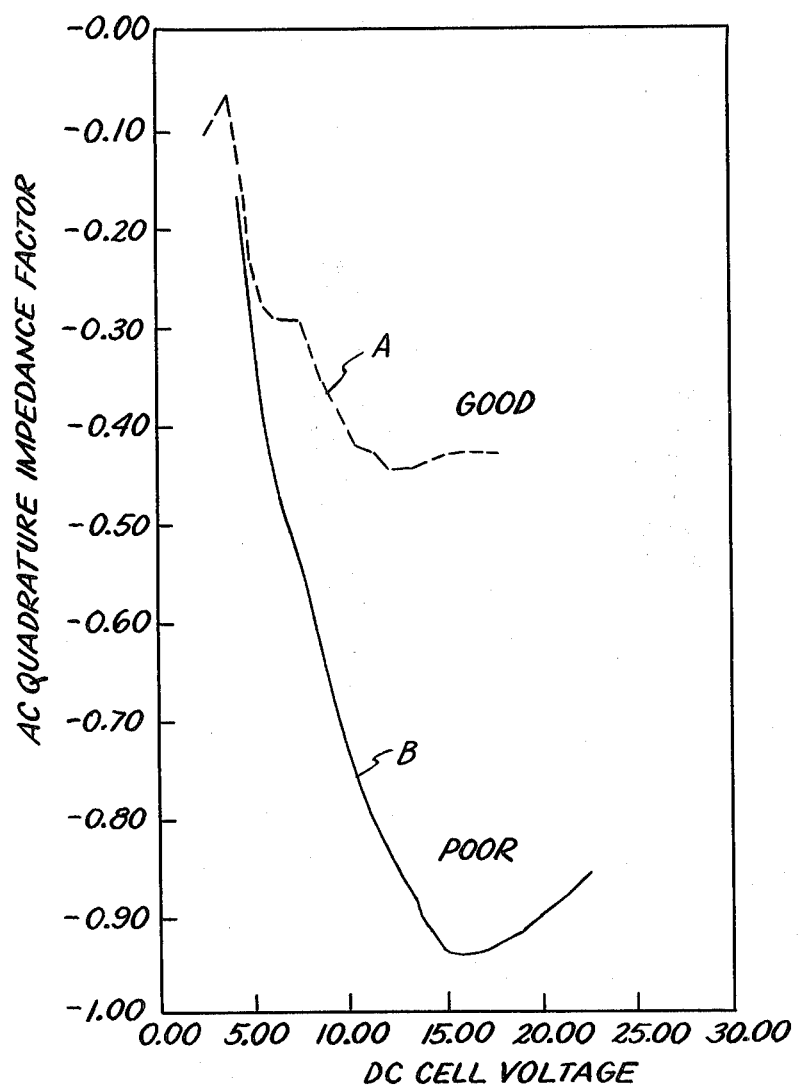

In order to provide a second electrochemical indicator, function generator 22 (e.g., Wavetech Model 171 Synthesizer/Function Generator) is electrically connected to d-c power supply 17 and supplies to the d-c power supply an a-c voltage. As a result, when generator 22 is operative, the d-c current supplied to cell 11 by power supply 17 will have the a-c current superimposed thereon. Thus, when this occurs, cell 11 will exhibit (in addition to the aforementioned d-c voltage response versus time) a change in the a-c quadrature component of the a-c cell voltage, which is out of phase with the a-c current, and an in-phase component of the a-c voltage. By employing phase sensitive detector 23 (e.g., Princeton Applied Research Model 129A Lock-in Amplifier) electrically connected across cell 11, the change in the a-c quadrature voltage component of the a-c cell voltage with time can be sensed (function generator 22 supplies a reference signal in phase with the a-c current to phase sensitive detector 23). These changes in the a-c quadrature voltage component as a function of time, or d-c voltage, are recorded as digital information by voltmeter 24 and data acquisition system 26 (e.g., the same as dc voltmeter 19 and system 21) having the capability to print out a graphic representation of this relationship as shown in FIG. 5. Actually by the use of a channel selector, or scanner (not shown), voltmeter 19 and system 21 with proper connections can be used to function in sequence first, as voltmeter 19 and system 21 and second, as voltmeter 24 and system 26, and repeating this sequence, thereby storing both kinds of data.

Instead of monitoring the a-c quadrature voltage component, similar results could be obtained by monitoring the amplitude and phase angle of the a-c cell voltage. As will be described in connection with FIG. 5, the relationship between the quadrature voltage component of the a-c cell voltage over time will exhibit a minimum. The value of the depth of that minimum (i.e., a measurement from zero) recorded after a d-c cell voltage of at least eight volts has been reached, provides a second electrochemical parameter in the practice of the process of this invention.

As noted hereinabove, the combination of recorder 18, voltmeter 19 and data acquisition system 21 in addition to providing information on the change in d-c cell voltage occasioned by the step-change in applied d-c current, also serves to determine a third electrochemical indicator; namely, the degree of non-linearity in the relationship between d-c cell voltage and time as d-c current continues to be applied in the absence of a-c current.

One version of apparatus for use in a simpler (e.g., fewer electrochemical parameters recorded) test procedure is set forth in FIG. 2. As may be seen by comparing FIG. 2 with FIG. 1, the only components employed are those supplying d-c current and sensing and recording d-c cell voltage as a function of time. As will be described in connection with FIG. 4, this simpler equipment arrangement serves to provide two of the three electrochemical parameters obtained with the equipment of FIG. 1.

Treatment of the zirconium-base alloy surface prior to electrochemical testing thereof has typically included mechanical abrading with wet 600 grit emery paper followed by a 90-second etch (i.e., chemical polishing) in the following solution formulation:
650 volume parts of 58% by wt. $HNO_3$
23 volume parts of 70% by wt. HF
828 volume parts of water.
The mechanical abrasion is, however, optional and the extent of the desired chemical polish should be determined by routine test. Shorter times (e.g., 60 seconds) coupled with gentle agitation have been successfully employed. Too short a period of chemical etch will be accompanied by poor a-c impedance stability; too long an etch will result in unnecessary material loss. Other etch formulations are within the skill of the art.

Figure 3:
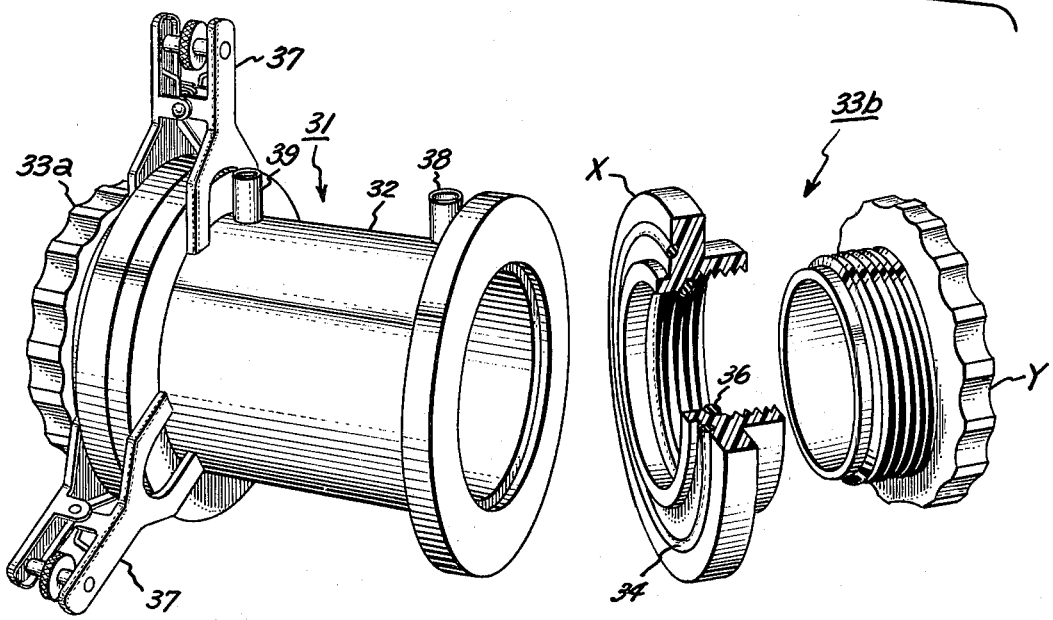
FIG. 3 is a three-dimensional view partially cut away of the preferred construction of the device designed to cooperate with the outer surface of a tubular body of zirconium-base alloy in the conduct of the electrochemical tests of this invention.

A particularly effective device for defining a leak-tight volume to function as electrochemical cell 11, schematically illustrated in FIGS. 1 and 2, is shown partially disassembled and cut away in FIG. 3. The device 31 comprises an electrically conducting portion comprising metal component 32, and electrically non-conducting portions comprising the closures 33a and 33b, the latter being shown disassembled and partially cut away. Device 31 is adapted to cooperate with the outside surface of a tubular body (not shown) of a zirconium-base alloy, such as a tubeshell or fuel cladding, and defines therewith the structural and functional components of an electrochemical cell. The construction is such that the area of the tubular member enclosed within the electrochemical cell is a constant and sealing of device 31 against the tubular member ensures that there will be no leakage of electrolyte. The connections between closures 33a, 33b and metal component 32 are facilitated by appropriate flanging as shown. Further description of the end closure construction will be provided only for closure 33b, it being understood that the construction of closure 33a is a duplicate thereof. Liquid-tight sealing between parts 33b and metal component 32 is provided by O-ring 34 seated in an appropriate groove. Liquid-tight sealing between closure 33b and the surface of the metal tubular member is provided by O-ring 36, which is forced into sealing engagement by tightening of the threaded connection between plastic parts X and Y. Parts X and Y together with O-rings 34 and 36 comprise closure 33b. Although the interconnection between the flanges of the insulating closures and the electrically conducting metal component can be made by the use of various fasteners (e.g., bolts or screws), the preferred method is the use of several spring clamps 37 (two shown) to facilitate quick disassembly.

In addition to their obvious structural functions, component 32 and closures 33a, 33b each have an additional function in the electrolytic cell as noted below. Passageways 38 and 39 offer access to the internal volume to be defined between housing device 31 and the surface of the metal member encircled thereby. In its simplest manner to use, device 31 is slipped over the end of a tubular alloy body to be tested, after chemically polishing the area to be covered. All sealing arrangements are made liquid-tight; electrolyte (preferably dilute sulfuric acid about 0.25 molar), is introduced to fill the cavity so defined, and electrical connections are appropriately made to interconnect metallic housing component 32 (electrically insulated from the alloy body by closures 33a and 33b), d-c power supply 17 and the alloy body, such that the surface area of the alloy body defined within housing 31 will be the anode of electrolytic cell 11, when d-c current is imposed. The testing proceeds as will be described in connection with FIGS. 4 and 5 and, thereafter, the electrolyte is removed, the sealing means are relaxed and device 31 is removed from the tubular member, which is then washed, and replaced by another tubular member to be tested.

Although device 31 is constructed to cooperate with the outer surface of a tubular member, devices functioning in the same way can be readily constructed for the testing of other alloy shapes (e.g., plates or bars) using the principles set forth herein. Manifestly, all parts must be resistive to attack by the electrolyte. Component 32 is preferably made of stainless steel or nickel. Closures 33a, 33b are preferably made of a machinable plastic strong enough to provide support for a good liquid-tight seal. Plastics typically also provide the requisite electrically insulating qualities. The O-rings are of elastomeric material and, preferably, of a fluorocarbon elastomer containing a tetrafluoroethylene additive (e.g., FETFE O-rings by Ace Glass, Inc., Vineland, N.J.).

Once the electrolytic cell 11 has been established with proper electrical connections made thereto, the rest of the process of this invention is conducted by applying to the cell a constant direct current having a value such as will provide a current density at the anode in the range of from about 0.1 milliamperes per square centimeter (mA/cm$^2$) d-c to about 10 mA/cm$^2$ d-c. In the process, which can be conducted using the equipment of FIG. 1, a constant alternating current is superimposed on the d-c current applied to the electrolytic cell. The level of a-c current providing a current density at the anode in the range of from about 0.1 percent to 10 percent of the current density of the d-c current is employed. In this range of a-c current, the signal-to-noise ratio encountered with the usual commercial equipment is adequate. The frequency of the a-c current applied should be in the range of from about 2 Hz to 60 Hz, preferably about 30 Hz. The quadrature component of the a-c cell voltage is monitored as a function of time and, after the d-c cell voltage has reached a value of at least eight volts, the depth of the minimum, which occurs in the relationship between the quadrature component of the a-c cell voltage and time, is measured. After this minimum has been sensed and recorded, the application of alternating current is ceased.

Typical curves reflecting the minimums in the quadrature component of the a-c cell voltage representative of Zircaloy-2 tubeshells with good nodular corrosion resistance (Curve A) and poor corrosion resistance (Curve B) are displayed in FIG. 5. The ordinate in FIG. 5 reflects a-c voltage response to the a-c current (1.0 volt d-c equals 10 mv (RMS) a-c) and, at least as a net value, is directly related to the capacitance of cell 11. Since d-c cell voltage increases with time, FIG. 5 basically represents the relationship between a-c quadrature voltage component and time.

Once the alternating current has been cut off, the constant d-c current previously applied is decreased by a step-change to a constant value providing a current density of less than one-half the direct current density previously utilized. When this change in current density is made, the d-c cell voltage response as a function of time will exhibit a transient. It is necessary as part of the evaluation procedure to record this transient. The d-c cell voltage response as a function of time is monitored from the onset of the application of d-c current and recorded digitally. Although this relationship can also be graphically displayed from the onset of the application of d-c current, it should at least be graphically displayed from the time the step-change occurs until the cell voltage, which has dropped during the transient, again starts to rise. The transient can be accurately measured from the graph.

In making the step-change in d-c current, the value of the current is preferably dropped to about one-fifth its earlier value with a preferred range of from about one-third to one-tenth the initial value, and as an operable range, from one-fifteenth to less than one-half the initial value. The selection of the starting d-c current density depends upon the capability of the equipment employed. Thus, it depends upon the frequency of data acquisition in comparison to the length of time required to accumulate the data. If the time required for needed data acquisition is unreasonably long, then better equipment (i.e., capable of faster data acquisition) should be employed. A workable test value for current density employing the equipment identified herein lies in the 0.4 mA/cm$^2$–0.6 mA/cm$^2$ range. Referring to FIG. 4, Curves C and D reflect the d-c cell voltage-versus-time relationships for tubeshells having good and poor nodular corrosion resistance, respectively. The parameter of interest in these curves is the measure of the transient (i.e., the vertical drop shown by dimension) occurring after the step-change in applied d-c voltage was made.

Up to this point in the process, two electrochemical kinetic evaluations have been made. Still a third evaluation is made as a continuation of the process described hereinabove. After the transient has been monitored and the cell voltage again starts to increase in value, the applied constant d-c current continues or, preferably, is increased to a higher value, not necessarily the same as the initial constant d-c current applied, such that a current density is established at the anode in the range of from about 0.1 mA/cm$^2$ d-c to about 10 mA/cm$^2$ d-c and the variation of d-c cell voltage versus time is monitored in order to determine the degree of non-linearity occurring in this relationship as the thickness of the oxide layer increases at higher voltages. As may be seen in FIG. 4 presenting typical curves obtained with Zircaloy-2 tubeshell materials, material having poor nodular corrosion resistance will exhibit a linear, or near-linear response (Curve E), while material having good nodular corrosion resistance exhibits a distinct non-linear response (Curve F).

Different methods can be used to determine the degree of non-linearity. As mentioned hereinabove, one approach is to program the computer digitally storing the values of d-c cell voltage as a function of time to calculate the slope of the d-c cell voltage versus time curve at two preselected points spaced sufficiently far apart (e.g., at 35 volts and 75 volts) and then to take the ratio of these slopes. The resulting figure provides a quantitative indication of curvature.

The series of values obtained (d-c cell voltage transient, a-c cell voltage quadrature component and degree of non-linearity) are then compared with standardized values to assess the corrosion susceptibility of that particular alloy body.

Standardized values can, of course, be determined by subjecting a sample cut from each of a series of tubeshells to testing in an operating boiling water reactor and testing the same series of tubeshells by the method of this invention and then correlating the nodule density developed on the reactor-exposed samples to the test results by the practice of this invention. Such an approach, however, requires a great deal of time.

Figure 6:
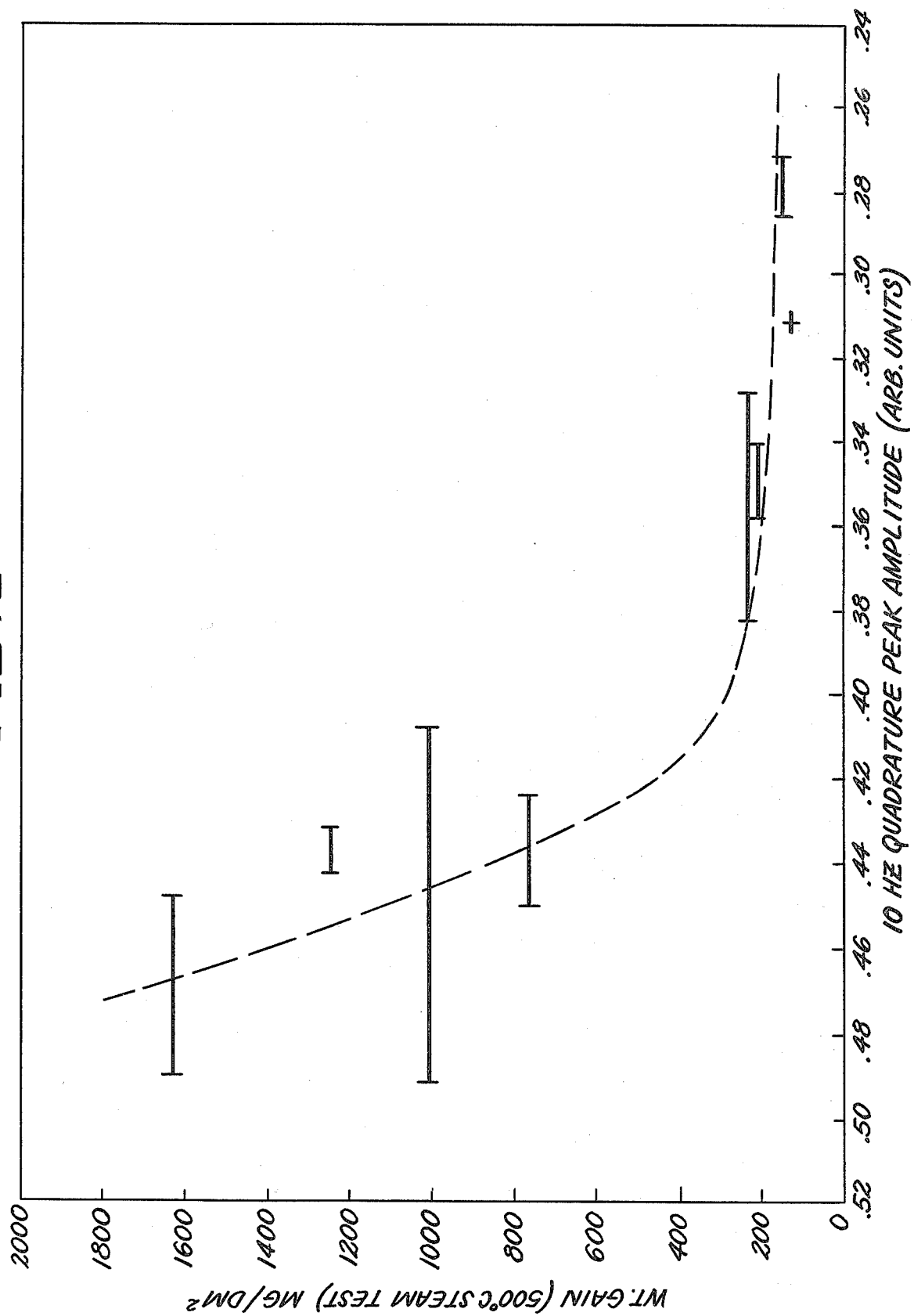
Figure 7:
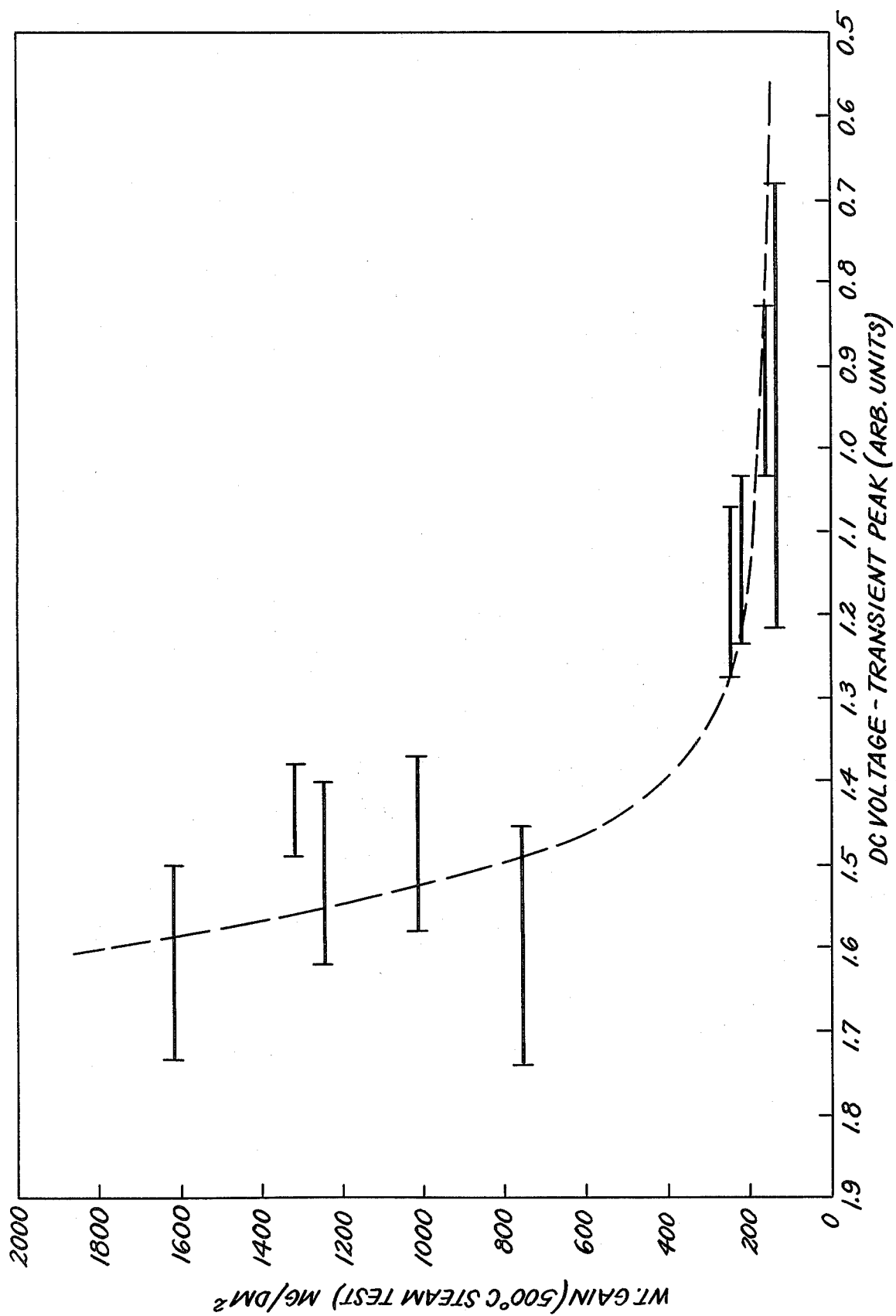

A more convenient approach is to correlate with the weight gain results obtained in the aforementioned 500° C. steam test. Thus, a series of tubeshells (or fuel claddings) are identified, which are known to have a range of resistances to nodular corrosion ranging from "very good" to "very poor" as evidenced by steam tests conducted on a sample from each tubeshell. These samples will, therefore, have known (or determinable) weight gains. The tubeshells from which the samples were taken are then subjected to test by the practice of this invention. Graphs correlating weight gains in the steam test with each of the electrochemical kinetic parameters determined for the comparable tubeshells can then be plotted. Curves can then be plotted whereby for a given numerical value representing the electrochemical response (e.g., d-c cell voltage transient 0.5 inches long) of a particular tubeshell a comparable value of weight gain will apply. Examples of such curves are shown in FIGS. 6, 7 and 8. It is left to the individual user of this invention to assess a particular value for the rejection threshold. Similar curves can be routinely prepared for other electrode configurations of other zirconium-base alloys for which anodic oxidation exhibits the same electrochemical behavior.

The horizontal bar-like representation in each of FIGS. 6, 7 and 8 in almost all instances interconnect two slightly different results such as can be expected at spaced locations along the same tubeshell.

The following parametric values have been found to represent a good compromise among speed, sensitivity and accuracy utilizing the device of FIG. 3 for the testing of Zircaloy-2 tubeshell:

| | |
|---|---|
| Nominal O.D. | 2.50 inches |
| Anode area | 265 cm$^2$ |
| Initial constant d-c current | 150 mA |
| Constant a-c current | 1.2 mA (RMS), 30 Hz |
| Step-change at | 27 volts |
| Constant d-c current after step-change | 30 mA (a-c signal off) |
| Constant d-c current after transient | 150 mA |
| Maximum d-c cell voltage | ~80 volts |
| Electrolyte | 0.25M H$_2$SO$_4$ |

The less rigid method described hereinabove, which does not utilize the quadrature component of the a-c cell voltage, would be conducted in the manner described hereinabove for the three-parameter electrochemical assay.

This invention, therefore, by the utilization of electrochemical kinetic information provides a new approach to non-destructive corrosion susceptibility screening.

What I claim as new and desire to secure by Letters Patent of the United States is:

1. Apparatus for generating and recording specific electrochemical kinetic information in order to characterize the susceptibility of a zirconium-base alloy body to nodular corrosion, comprising in combination:
    means adapted to releasably cooperate with a predetermined area of said alloy body to define a liquid-tight volume therewith, said defining means having inlet means and outlet means in flow communication with said volume and also including electrically conducting structure disposed to be spaced and electrically insulated from said pre-determined area,
    means electrically connected to said electrically conducting structure and also adapted to be electrically connected to said pre-determined area for supplying constant d-c current therebetween at pre-selected levels of current with said pre-determined area being at more positive electrical potential than said electrically conducting structure, and
    means electrically connected to said electrically conducting structure and also adapted to be electrically connected to said pre-determined area for sensing and recording the d-c voltage drop occurring between said electrically conducting structure and said pre-determined area as a function of time, when constant d-c current is applied therebetween.

2. The apparatus of claim 1 wherein the defining means comprises wall area and sealing means disposed between said wall area and the alloy body, the electrically conducting structure comprising a metallic portion of said wall area.

3. The apparatus of claim 2 wherein the metallic portion of the wall area is stainless steel.

4. The apparatus of claim 2 wherein the sealing means is elastomeric.

5. The apparatus of claim 4 wherein the elastomeric sealing means is made of hydrophobic material.

6. The apparatus of claim 5 wherein the hydrophobic material is a fluoroelastomer containing polytetrafluoroethylene as an additive.

7. The apparatus of claim 1 wherein the defining means is in a generally cylindrical configuration adapted to releasably cooperate with a cylindrical alloy body.

8. Apparatus for generating and recording specific electrochemical kinetic information in order to characterize the susceptibility of a zirconium-base alloy body to nodular corrosion, comprising in combination:
    means adapted to releasably cooperate with a predetermined area of said alloy body to define a liquid-tight volume therewith, said defining means having inlet means and outlet means in flow communication with said volume and also including electrically conducting structure disposed to be spaced and electrically insulated from said pre-determined area, means electrically connected to said electrically conducting structure and also adapted to be electrically connected to said pre-determined area for supplying constant d-c current therebetween at pre-selected levels of current with said pre-determined area being at a more positive electrical potential than said electrically conducting structure, means electrically connected to said electrically conducting structure and also adapted to be electrically connected to said pre-determined area for sensing and recording the d-c voltage drop occurring as a function of time between said electrically conducting structure and said pre-determined area, when d-c current is applied therebetween, means for selectively applying an a-c current to said means for supplying constant d-c current whereby an a-c current is superimposed on the d-c current supplied thereby and means electrically connected to said electrically conducting structure and also adapted to be electrically connected to said pre-determined area for sensing and recording the a-c quadrature component of the a-c voltage occurring as a function of time between said electrically conducting structure and said pre-determined area, when d-c current with superimposed a-c current is applied therebetween, said means for sensing and recording the a-c quadrature component of the a-c voltage being electrically connected to said a-c current applying means to receive a reference a-c signal therefrom.

9. The apparatus of claim 8 wherein the means for sensing and recording the a-c quadrature component comprises a phase-sensitive detector, a voltmeter and a data acquisition system electrically connected thereto.

10. The apparatus of claim 8 wherein the defining means comprises wall area and sealing means disposed between said wall area and the alloy body, the electrically conducting structure comprising a metallic portion of said wall area.

11. The apparatus of claim 10 wherein the metallic portion of the wall area is stainless steel.

12. The apparatus of claim 10 wherein the sealing means is elastomeric.

13. The apparatus of claim 12 wherein the elastomeric sealing means is made of hydrophobic material.

14. The apparatus of claim 13 wherein the hydrophobic material is a fluoroelastomer containing polytetrafluoroethylene as an additive.

15. The apparatus of claim 8 wherein the defining means is in a generally cylindrical configuration adapted to releasably cooperate with a cylindrical alloy body.

16. An electrochemical process for predicting the ability of a zirconium-base alloy body to resist nodular corrosion in a boiling water nuclear reactor during normal operation, comprising the steps of:

(1) chemically polishing a pre-determined area of a surface of said alloy body, (2) making said pre-determined area the anode in an electrochemical cell, (3) applying to said cell constant direct current providing a current density at the anode in the range of from about 0.1 mA/cm$^2$ d-c to about 10 mA/cm$^2$ d-c, (4) decreasing the constant direct current previously applied to said cell by a step-change to a constant value providing a current density of less than one-half the direct current density utilized in step (3) and monitoring the d-c cell voltage response, which exhibits a transient, as a function of time until the cell voltage again starts to increase in value, (5) re-applying to said cell a value of constant direct current providing a current density in the range of from 0.1 mA/cm$^2$ d-c to about 10 mA/cm$^2$ d-c and measuring the degree of non-linearity occurring in the relationship between d-c voltage and time, (6) measuring the value of the transient voltage, the depth of the minimum occurring as the d-c cell voltage varies with time, (7) comparing the values obtained in steps (5) and (6) to standardized values to determine the corrosion susceptibility of said alloy body.

17. The process recited in claim 16 wherein the ratio of the initial constant direct current to the constant direct current applied after the step-change is about 5:1.

18. The process of claim 16 wherein the zirconium-base alloy is Zircaloy-2.

19. The process of claim 16 wherein the initial direct current density at the anode is about 0.5 mA/cm$^2$.

20. An electrochemical process for predicting the ability of a zirconium-base alloy body to resist nodular corrosion in a boiling water nuclear reactor during normal operation, comprising the steps of:

(1) chemically polishing a pre-determined area of a surface of said alloy body, (2) making said pre-determined area the anode in an electrochemical cell, (3) applying to said cell constant direct current providing a current density at the anode in the range of from about 0.1 mA/cm$^2$ d-c to about 10 mA/cm$^2$ d-c and simultaneously applying to said cell alternating current providing a current density at the anode having a workable signal-to-noise ratio and monitoring the quadrature component of the a-c cell voltage response thereto as a function of time, (4) measuring the value of the depth of the minimum occurring in the quadrature component of the a-c cell voltage-versus-time relationship after a d-c cell voltage of at least 8 volts has been reached, (5) ceasing the application of alternating current to said cell, (6) decreasing the constant direct current previously applied to said cell by a step-change to a constant value providing a current density of less than one-half the direct current density utilized in step (3) and monitoring the d-c cell voltage response, which exhibits a transient, as a function of time until the cell voltage again starts to increase in value, (7) re-applying to said cell a value of constant direct current providing a current density at the anode in the range of from about 0.1 mA/cm$^2$ d-c to about 10 mA/cm$^2$ d-c and measuring the degree of non-linearity occurring in the relationship between d-c cell voltage and time, (8) measuring the value of the transient voltage, the depth of the minimum occurring as the d-c cell voltage varies with time, (9) comparing the values obtained in steps (4), (7) and (8) to standardized values to determine the corrosion susceptibility of said alloy body.

21. The process of claim 20 wherein the alternating current density at the anode has a value in the range of from 0.1 percent to 10 percent of the initial d-c current density value.

22. The process recited in claim 20 wherein the ratio of the initial constant direct current to the constant direct current applied after the step-change is about 5:1.

23. The process of claim 20 wherein the applied a-c current has a frequency in the range of from about 2 Hz to about 60 Hz.

24. The process of claim 23 wherein the applied a-c current has a frequency of about 30 Hz.

25. The process of claim 20 wherein the zirconium-base alloy is Zircaloy-2.

26. The process of claim 20 wherein the initial direct current density at the anode is about 0.5 mA/cm$^2$.

27. An electrochemical process for predicting the ability of a zirconium-base alloy body to resist nodular corrosion in a boiling water nuclear reactor during normal operation, comprising the steps of:
(1) chemically polishing a pre-determined area of a surface of said alloy body,
(2) making said predetermined area the anode in an electrochemical cell,
(3) appplying constant d-c current, alone or with superimposed constant a-c current to said cell,
(4) determining at least one electrochemical kinetic parameter of said pre-determined area selected from the group consisting of (a) the minimum in the a-c quadrature voltage component of the a-c cell voltage, (b) the magnitude of the transient in the d-c cell voltage-versus-time relationship and (c) the degree of non-linearity in the d-c cell voltage-versus-time relationship, and
(5) comparing said at least one parameter to a standard for such parameter.

28. The process recited in claim 27 wherein constant d.c. current is applied to the electrochemical cell and the parameter determined is the magnitude of the transient in the d-c cell voltage-versus-time relationship.

29. The process recited in claim 27 wherein constant d.c. current with superimposed constant a.c. current is applied to the electrochemical cell and the parameter determined is the minimum in the a-c quadrature voltage component of the a-c cell voltage.

30. The process recited in claim 27 wherein constant d-c current is applied to the electrochemical cell and the parameter determined is the degree of non-linearity in the d-c cell voltage-versus-time relationship.

* * * * *